(12) United States Patent
Satoh et al.

(10) Patent No.: US 9,017,476 B2
(45) Date of Patent: Apr. 28, 2015

(54) MODIFIED METAL OXIDE SOL

(75) Inventors: Masahiro Satoh, Kyoto (JP); Satsuki Kitajima, Kyoto (JP); Daisaku Shojo, Kyoto (JP)

(73) Assignee: KRI, Inc., Kyoto-shi (JP)

( * ) Notice: Subject to any disclaimer, the term of this patent is extended or adjusted under 35 U.S.C. 154(b) by 280 days.

(21) Appl. No.: 13/695,979

(22) PCT Filed: May 11, 2011

(86) PCT No.: PCT/JP2011/002629
§ 371 (c)(1), (2), (4) Date: Nov. 2, 2012

(87) PCT Pub. No.: WO2011/142130
PCT Pub. Date: Nov. 17, 2011

(65) Prior Publication Data
US 2013/0055927 A1 Mar. 7, 2013

(30) Foreign Application Priority Data

May 14, 2010 (JP) ................................. 2010-111948

(51) Int. Cl.
*C08K 5/548* (2006.01)
*C09D 5/00* (2006.01)
*C08K 3/36* (2006.01)
*C09K 3/16* (2006.01)
*C07F 7/08* (2006.01)
*C08G 77/58* (2006.01)
*C09D 1/00* (2006.01)
*C09K 3/14* (2006.01)
*C07F 7/18* (2006.01)

(52) U.S. Cl.
CPC .............. *C07F 7/0856* (2013.01); *C08G 77/58* (2013.01); *C09D 1/00* (2013.01); *C09K 3/1463* (2013.01); *C07F 7/1836* (2013.01)

(58) Field of Classification Search
None
See application file for complete search history.

(56) References Cited

U.S. PATENT DOCUMENTS

| 2007/0099035 | A1 | 5/2007 | Li et al. | |
| 2010/0092765 | A1* | 4/2010 | Hager et al. | 428/331 |
| 2010/0209946 | A1* | 8/2010 | Jing et al. | 435/7.33 |
| 2011/0301375 | A1* | 12/2011 | Iwai et al. | 556/451 |
| 2013/0071649 | A1* | 3/2013 | Hager et al. | 428/331 |

FOREIGN PATENT DOCUMENTS

| JP | 6-100695 A | 4/1994 |
| JP | 9-301742 A | 11/1997 |
| JP | 2001-040283 A | 2/2001 |
| JP | 2005-042053 A | 2/2005 |
| JP | 2007-504637 A | 3/2007 |
| JP | 2009-203185 A | 9/2009 |
| JP | 2010-269985 A | 12/2010 |

OTHER PUBLICATIONS

English-language machine-generated translation of JP-2009203185, translation generated Aug. 2014, 16 pages.*
Badley et al. "Silica-Bound Sulfonic Acid Catalysts" J. Org. Chem. 1989, 54, 5437-5443.*
International Search Report for PCT/JP2011/002629, mailing date of Aug. 16, 2011.

* cited by examiner

*Primary Examiner* — Robert S Loewe
(74) *Attorney, Agent, or Firm* — Westerman, Hattori, Daniels & Adrian, LLP

(57) ABSTRACT

Disclosed is a modified metal oxide sol that has a large hydrophilizing effect and antistatic effect, can be produced at low cost and is capable of being a coating. Specifically disclosed is a modified metal oxide sol characterized by modification by a functional group represented by formula (1) at 0.55-5.5 mmol per 1 g of metal oxide sol. $MOS(=O)_2-R^1-Si(CH_3)_n(-O-)_{3-n}$ (1) {In the formula, M is a hydrogen ion, $C_{1-4}$ alkyl group, metal ion or ammonium ($NR^2_4$) group; $R^1$ is a $C_{1-10}$ alkylene group (may have urethane bonds or urea bonds in the main alkylene chain); $R^2$ may be the same or different and is a $C_{1-5}$ alkyl group or a hydrogen atom; and n represents 0 or 1}.

9 Claims, No Drawings

MODIFIED METAL OXIDE SOL

TECHNICAL FIELD

The present invention relates to a modified metal oxide sol that has a large hydrophilizing effect and antistatic effect, and can be produced at low costs and is capable of being a coating. The present invention relates more specifically to a modified metal oxide sol suitable as a hydrophilizing agent, an antistatic agent, a hydrophilic coating composition, an antibacterial agent, an electroconductive coating agent or an ion (proton) conductive coating agent.

BACKGROUND ART

As a surface hydrophilizing agent, known is a compound obtained by an ene-thiol reaction between a vinyl compound having a sulfonic acid group and a compound having a thiol group (Patent Document 1).

Known is also a sulfonic-acid-group-modified anionic silica sol for use in a CMP polishing agent (Patent Document 2).

PRIOR ART DOCUMENTS

Patent Documents

Patent Document 1: JP-A-2009-203185
Patent Document 2: JP-A-2010-269985

SUMMARY OF THE INVENTION

Problems to be Solved by the Invention

However, with respect to a conventional surface hydrophilizing agent prepared from a compound obtained by an ene-thiol reaction between a vinyl compound having a sulfonic acid group and a compound having a thiol group, there remains a problem that the vinyl compound, which is a starting material, is high in costs so that costs are increased. Moreover, a sulfonic-acid-group-modified anionic silica sol for use in a CMP polishing agent is small in the content of sulfonic acid groups to be insufficient in antistatic performance, and is also insufficient in strength as a coating film. An object of the present invention is to provide a modified metal oxide sol suitable as a hydrophilizing agent, an antistatic agent, a hydrophilic coating composition, an antibacterial agent, an electroconductive coating agent or an ion (proton) conductive coating agent.

Solutions to the Problems

In order to solve the above-described problems, the present inventors have made eager investigations to accomplish the present invention. Accordingly, the present invention is a modified metal oxide sol wherein a metal oxide sol is modified with a functional group represented by the following formula (1) in an amount of 0.55 mmol or more per gram of the sol:

$$MOS(=O)_2-R^1-Si(CH_3)_n(-O-)_{3-n} \quad (1)$$

{wherein M is a hydrogen ion, an alkyl group having 1 to 4 carbon atoms, a metal ion, or an ammonium ($NR^2_4$) group, $R^1$ is an alkylene group having 1 to 10 carbon atoms (optionally having a urethane bond or a urea bond in the present alkylene chain), $R^2$s, which may be the same or different, are each an alkyl group having 1 to 5 carbon atoms or a hydrogen atom, and n represents 0 or 1}.

The present invention is also a hydrophilizing agent comprising the above-described modified metal oxide sol.

The present invention is also a hydrophilic coating composition comprising the above-described modified metal oxide sol.

The present invention is also a structural body obtained by coating with the above-described hydrophilic coating composition, and then curing the composition.

The present invention is also an antistatic agent comprising a solid obtained by drying the above-described modified metal oxide sol.

The present invention is also a structural body comprising the above-described antistatic agent.

Effects of the Invention

The present invention makes it possible to provide a modified metal oxide sol that has a large hydrophilizing effect and antistatic effect, and can be produced at low costs and is capable of being a coating.

MODE FOR CARRYING OUT THE INVENTION

In the present invention, the modified metal oxide sol is modified with a functional group represented by the following formula (1):

$$MOS(=O)_2-R^1-Si(CH_3)_n(-O-)_{3-n} \quad (1)$$

{wherein M is a hydrogen ion, an alkyl group having 1 to 4 carbon atoms, a metal ion, or an ammonium ($NR^2_4$) group, $R^1$ is an alkylene group having 1 to 10 carbon atoms (optionally having a urethane bond or a urea bond in the present alkylene chain), $R^2$s, which may be the same or different, are each an alkyl group having 1 to 5 carbon atoms or a hydrogen atom, and n represent 0 or 1}.

In the above-described formula (1), examples of the alkylene group having 1 to 10 carbon atoms of $R^1$ include a methylene group, an ethylene group, a propylene group, a butylene group and a pentylene group. Of these groups, preferred is a propylene group, considering costs and availability of starting materials.

Examples of M include a hydrogen ion, an alkyl group having 1 to 4 carbon atoms, metal ions (such as alkali metal ions, alkaline earth metal ions, silver ions, copper ions, and nickel ions), and ammonium ($NR^2_4$) ions. Preferred are a hydrogen ion, alkali metal ions, alkaline earth metal ions, silver ions and ammonium ions, considering hydrophilicity, antibacterial activity, and others.

Examples of $R^2$s in the ammonium ion include a hydrogen atom and an alkyl group having 1 to 5 carbon atoms.

Preferred are a hydrogen atom and alkyl groups each having 1 to 2 carbon atoms (a methyl group and an ethyl group). $R^e$s may be the same or different.

Examples of the alkali metal ions and the alkaline earth metal ions include a lithium ion, a sodium ion, a potassium ion, a cesium ion, a magnesium ion, and a calcium ion.

Of these ions, preferred is an alkali metal ion, and particularly preferred is a lithium ion or a sodium ion.

Specific examples of the functional group represented by the formula (1) include the following:

$HOSO_2-CH_2CH_2CH_2Si(-O-)_3LiOSO_2-$
$CH_2CH_2CH_2Si(-O-)_3NaOSO_2-$
$CH_2CH_2CH_2Si(-O-)_3KOSO_2-$
$CH_2CH_2CH_2Si(-O-)_3NH_4OSO_2-$

CH₂CH₂CH₂Si(—O—)₃N(CH₃)₄OSO₂—
CH₂CH₂CH₂CH₂Si(—O—)₃NH(C₂H₅)₃OSO₂—
CH₂CH₂CH₂Si(—O—)₃AgOSO₂—
CH₂CH₂CH₂Si(—O—)₃HOSO₂—
CH₂C₂OCONHCH₂CH₂CH₂Si(—O—)₃LiOSO₂—
CH₂CH₂OCONHCH₂CH₂CH₂Si(—O—)₃NaOSO₂—
CH₂CH₂OCONHCH₂CH₂CH₂Si(—O—)₃KOSO₂—
CH₂CH₂OCONHCH₂CH₂CH₂Si(—O—)₃NH₄OSO₂—
CH₂CH₂OCONHCH₂CH₂CH₂Si(—O—)₃N(CH₃)₄OSO₂—CH₂CH₂OCONHCH₂CH₂CH₂Si(—O—)₃NH(C₂H₃)₃OSO₂—
CH₂CH₂OCONHCH₂CH₂CH₂Si(—O—)₃AgOSO₂—
CH₂CH₂OCONHCH₂CH₂CH₂Si(—O—)₃HOSO₄—
CH₂CH₂NHCONHCH₂CH₂CH₂Si(—O—)₃LiOSO₂—
CH₂CH₂NHCONHCH₂CH₂CH₂Si(—O—)₃NaOSO₂—
CH₂CH₂NHCONHCH₂CH₂CH₂Si(—O—)₃KOSO₂—
CH₂CH₂NHCONHCH₂CH₂CH₂Si(—O—)₃NH₄OSO₂—
CH₂CH₂NHCONHCH₂CH₂CH₂Si(—O—)₃N(CH₃)₄OSO₂—
CH₂CH₂NHCONHCH₂CH₂CH₂Si(—O—)₃NH(C₂H₃)₃OSO₂—
CH₂CH₂NHCONHCH₂CH₂CH₂Si(—O—)₃AgOSO₂—
CH₂CH₂NHCONHCH₂CH₂CH₂Si(—O—)HOSO₂—C₆H₄NHCONHCH₂CH₂Si(—O—)₃LiOSO₂—
CH₆H₄NHCONHCH₂CH₂CH₂Si(—O—)₃NaOSO₂—
C₆H₄NHCONHCH₂CH₂CH₂Si(—O—)₃KOSO₂—
C₆H₄NHCONHCH₂CH₂CH₂Si(—O—)₃NH₄OSO₂—
C₆H₄NHCONHCH₂CH₂CH₂Si(—O—)₃N(CH₃)₄OSO₂—C₆H₄NHCONHCH₂CH₂CH₂Si(—O—)₃NH(C₂H₆)₃OSO₂—
C₆H₄NHCONHCH₂CH₂CH₂Si(—O—)₃AgOSO₂—
C₆H₄NHCONHCH₂CH₂CH₂Si(—O—)₃   [Chemical Formula 1]

HOSO₂—CH₂CH₂CH₂SiCH₃(—O—)₂LiOSO₂—
CH₂CH₂CH₂SiCH₃(—O—)₂NaOSO₂—
CH₂CH₂CH₂SiCH₃(—O—)₂KOSO₂—
CH₂CH₂CH₂SiCH₃(—O—)₂NH₄OSO₂—
CH₂CH₂CH₂SiCH₃(—O—)₂NH(CH₃)₃OSO₂—
CH₂CH₂CH₂SiCH₃(—O—)₂NH(C₂H₅)₃OSO₂—
CH₂CH₂CH₂SiCH₃(—O—)₂AgOSO₂—
CH₂CH₂CH₂SiCH₃(—O—)₂HOSO₂—
CH₂CH₂OCONHCH₂CH₂CH₂SiCH₃(—O—)₂LiOSO₂—
CH₂CH₂OCONHCH₂CH₂CH₂SiCH₃(—O—)₂NaOSO₂—
CH₂CH₂OCONHCH₂CH₂CH₂SiCH₃(—O—)₂KOSO₂—
CH₂CH₂OCONHCH₂CH₂CH₂SiCH₃(—O—)₂NH₄OSO₂—
CH₂CH₂OCONHCH₂CH₂CH₂SiCH₃(—O—)₂NH(CH₃)₃OSO₂—
CH₂CH₂OCONHCH₂CH₂CH₂SiCH₃(—O—)₂NH(C₂H₅)₃OSO₂—
CH₂CH₂OCONHCH₂CH₂CH₂SiCH₃(—O—)₂AgOSO₂—
CH₂CH₂OCONHCH₂CH₂CH₂SiCH₃(—O—)₂HOSO₂—
CH₂CH₂NHCONHCH₂CH₂CH₂SiCH₃(—O—)₂LiOSO₂—
CH₂CH₂NHCONHCH₂CH₂CH₂SiCH₃(—O—)₂NaOSO₂—
CH₂CH₂NHCONHCH₂CH₂CH₂SiCH₃(—O—)₂KOSO₂—
CH₂CH₂NHCONHCH₂CH₂CH₂SiCH₃(—O—)₂NH₄OSO₂—
CH₂CH₂NHCONHCH₂CH₂CH₂SiCH₃(—O—)₂NH(CH₃)₃OSO₂—
CH₂CH₂NHCONHCH₂CH₂CH₂SiCH₃(—O—)₂NH(C₂H₅)₃OSO₂—
CH₂CH₂NHCONHCH₂CH₂CH₂SiCH₃(—O—)₂AgOSO₂—
CH₂CH₂NHCONHCH₂CH₂CH₂SiCH₃(—O—)₂HOSO₂—
C₆H₄NHCONHCH₂CH₂CH₂SiCH₃(—O—)₂LiOSO₂—
C₆H₄NHCONHCH₂CH₂CH₂SiCH₃(—O—)₂NaOSO₂—
C₆H₄NHCONHCH₂CH₂CH₂SiCH₃(—O—)₂KOSO₂—
C₅H₄NHCONHCH₂CH₂CH₂SiCH₃(—O—)₂NH₄OSO₂—
C₆H₄NHCONHCH₂CH₂CH₂SiCH₃(—O—)₂NH(CH₃)₃OSO₂—
C₆H₄NHCONHCH₂CH₂CH₂SiCH₃(—O—)₂NH(C₂H₅)₃OSO₂—
C₆H₄NHCONHCH₂CH₂CH₂SiCH₃(—O—)₂AgOSO₂—
C₆H₄NHCONHCH₂CH₂CH₂SiCH₃(—O—)₂   [Chemical Formula 2]

Examples of the metal oxide sol include a silica sol, an alumina sol, and a zirconia sol.

Of these sols, preferred is a silica sol, and particularly preferred is an organosilica sol.

The organosilica sol is a colloidal solution in which colloidal silica having a surface modified at a nano-level is stably dispersed in an organic solvent. The organosilica sol can be dispersed in various organic solvents, such as alcohol, ketone, ether and toluene.

Specific examples thereof include organosilica sols manufactured by Nissan Chemical Industries, Ltd. (methanol silica sol, IPA-ST, IPA-ST, IPA-ST-UP, IPA-ST-ZL, EG-ST, NPC-ST-30, DMAC-ST, MEK-ST, MIBK-ST, PMA-ST, and PGM-ST), and high-purity organosilica sols manufactured by Fuyo Chemical Industries, Co., Ltd. (PL-1-IPA, PL-2L-PGME, and PL-2L-MEK).

These may be used alone or in combination of two or more thereof.

The modified metal oxide sol of the present invention is obtained by the following production method.

That is, the modified metal oxide sol is obtained by a method of adding, to a metal oxide sol, a silane coupling agent represented by the following formula (SC1) or (SC2) and having a functional group chemically convertible to a sulfonic acid group to cause the above-described silane coupling agent to react with silanol on the metal oxide sol, subsequently converting a thiol group to a sulfonic acid group, and optionally neutralizing the resultant with a metal salt.

[Chemical Formula 3]

$$HS-R^1-Si(CH_3)_n(-Y)_{3-n} \quad (SC1)$$

$$(Y-)_{3-n}(CH_3)SI-R_1-S-S-R_1-Si(CH_3)_n(-Y)_{3-n} \quad (SC2)$$

{in each of the formula, $R^1$ is an alkylene group having 1 to 10 carbon atoms (optionally having a urethane bond or a urea bond in the present alkylene chain), Ys, which may be the same or different, each represent an alkoxy group having 1 to 4 carbon atoms or a hydroxyl group, and n represents 0 or 1}.

Specific examples of the silane coupling agent represented by the formula (SC1) or (SC2) include the following:

HSCH₂CH₂CH₂Si(OCH₃)₃CH₃CH(HS)CH₂Si(OC₂H₅)₃HSCH₂CH₂Si(OCH₃)₃HSCH₂CH₂Si(OC₂H₅)₃HSCH₂CH₂OCONHCH₂CH₂CH₂Si(OC₂H₅)₃HSCH₂CH₂NHCONHCH₂CH₂CH₂Si(OC₂H₅)₃HSC₆H₄NHCONHCH₂CH₂CH₂Si(OC₂H₅)₃(OC₂H₅)₃SiCH₂CH₂CH₂—S—S—CH₂CH₂CH₂Si(OC₂H₅)₃   [Chemical Formula 4]

Of these compounds, a compound having a urethane bond or a urea bond can be obtained by causing 2-mercaptoethanol, 2-mercaptoethylamine or 4-mercaptoaniline to react with a silane coupling agent having an isocyanate group.

Examples of a solvent when the silane coupling agent is caused to react with the metal oxide sol include alcohol-based solvents such as methanol, ethanol, isopropanol, n-butanol, t-butanol, pentanol, ethylene glycol, propylene glycol and 1,4-butanediol, ether-based solvents such as diethyl ether, tetrahydrofuran and dioxane, ketone-based solvents such as acetone and methyl ethyl ketone, and aprotic solvents such as dimethylsulfoxide and N,N-dimethylformamide, and mixed solvents thereof.

Of these solvents, preferred are alcohol-based solvents. These solvents may be used alone or in combination of two or more thereof.

The concentration of the metal oxide sol, which is a starting material, relative to the solvent is from 1 to 50% by weight, and preferably from 1 to 30% by weight.

The amount of the silane coupling agent having a functional group chemically convertible to a sulfonic acid group relative to the metal oxide sol is from 0.55 to 5.5 mmol, and preferably from 2.0 to 5.0 mmol per gram of the metal oxide sol.

If the amount is less than 0.55 mmol, the concentration of sulfonic acid groups is too low so that the hydrophilicity and the antistatic performance are declined. If the amount is more than 5.5 mmol, the amount of silanol on the metal oxide is insufficient so that molecules of the above-described silane coupling agent may be unfavorably self-condensed or the film-formability may be unfavorably declined.

The temperature at the time of the addition of the coupling agent having a functional group chemically convertible to a sulfonic acid group is not limited, but is preferably from normal temperature (about 20° C.) to the boiling point.

The reaction temperature is not also limited, but is preferably from normal temperature (about 20° C.) to the boiling point.

The reaction time is not also limited, but is preferably from 10 minutes to 48 hours, and in particular preferably from 6 hours to 24 hours.

Examples of a peroxide include organic peroxides (such as peracetic acid, m-chloroperbenzoic acid, and benzoyl peroxide), and inorganic peroxides (such as ozone, hydrogen peroxide, and calcium peroxide). Of these peroxides, preferred are hydrogen peroxide and peracetic acid, and particularly preferred is hydrogen peroxide.

The peroxide can be charged at a time or in parts during the previous stage (step of bonding the silane coupling agent having a functional group chemically convertible to a sulfonic acid group to the metal oxide sol) of the production step.

The amount of the peroxide to be used is from 200 to 5000% by mol, preferably from 300 to 5000% by mol, and more preferably from 500 to 5000% by mol relative to the silane coupling agent having a functional group convertible to a sulfonic acid group.

The temperature at the time of the addition of the peroxide is not limited, but is preferably normal temperature (about 20° C.)

The reaction temperature is not also limited, but is preferably from normal temperature (about 20° C.) to the boiling point.

The reaction time is not also limited, either, but is preferably from 10 minutes to 48 hours, and in particular preferably from 6 hours to 24 hours.

Examples of a base include hydroxides (such as lithium hydroxide, sodium hydroxide, potassium hydroxide, cesium hydroxide, magnesium hydroxide and calcium hydroxide), acetic acid salts (such as lithium acetate, sodium acetate, potassium acetate, and silver acetate), metal oxides (such as silver oxide), ammonia, trimethylamine, triethylamine, tetramethylammonium hydroxide, and tetraethylammonium hydroxide.

The temperature at the time of the neutralization is not particularly limited. It may be allowable to perform the neutralization ordinarily at room temperature.

The base to be added may be added as it is, or may be added after diluted with a solvent (such as water).

The modified metal oxide sol of the present invention may contain at least one silicon-based compound represented by the following formula (2):

$$X\text{—}(R^3)_m\text{—}Si(CH_3)_n(\text{—}Y)_{3-n} \quad (2)$$

{wherein X is a functional group selected from the group consisting of linear or branched alkyl groups having 1 to 20 carbon atoms, a vinyl group, a thiol group, an amino group, a chlorine atom, an acrylic group, a methacrylic group, any alkyl ester group, a styryl group, a phenyl group, an imidazolyl group, a glycidoxy group, a 3,4-epoxycyclohexyl group, and a blocked isocyanate group, $R^3$ is an alkylene group having 1 to 5 carbon atoms, m is 0 or 1, Ys, which may be the same or different, each represent an alkoxy group having 1 to 4 carbon atoms or a hydroxyl group, and n represents 0 or 1}.

The modified metal oxide sol in which the silicon-based compound represented by the formula (2) is contained is obtained by the following method. The above-described silicon-based compound is usually subjected to a condensation reaction with silanol of the metal oxide sol.

That is, the modified metal oxide sol can be obtained by a method of adding the silicon-based compound represented by the formula (2) to a solution of the modified metal oxide sol modified with the functional group represented by the above-described formula (1) to cause a condensation reaction of the silicon-based compound with the silanol of the metal oxide sol.

Examples of the silicon-based compound represented by the formula (2) include the following:

$CH_3Si(OCH_3)_3 CH_3Si(OC_2H_5)_3 C_8H_{17}Si(OCH_3)_3 C_8H_{17}Si(OC_2H_5)_3 C_{18}H_{37}Si(OCH_3)_3 C_{18}H_{37}Si(O_2H_5)_3 CH_2\text{=}CHSi(OCH_3)_3 CH_2\text{=}CHSi(OC_2H_5)_3 H_2NCH_2CH_2CH_2Si(OCH_3)_3 H_2NCH_2CH_2CH_2Si(OC_2H_5)_3 ClCH_2CH_2CH_2Si(OCH_3)_3 SHCH_2CH_2CH_2Si(OCH_3)_3 SHCH_2CH_2CH_2Si(CH_3)(OCH_3)_2 CH_2\text{=}CHCOOCH_2CH_2CH_2Si(OCH_3)_3 CH_2\text{=}C(CH_3)COOCH_2CH_2CH_2Si(OCH_3)_3 C_6H_5Si(OCH_3)_3 C_6H_5Si(OC_2H_5)_3 (CH_3)_3COCOCH_2CH_2SCH_2CH_2CH_2Si(OCH_3)_3 (CH_3)_3COCOCH_2CH_2SCH_2CH_2CH_2(CH_3)Si(OCH_3)_2$ [Chemical Formula 5]

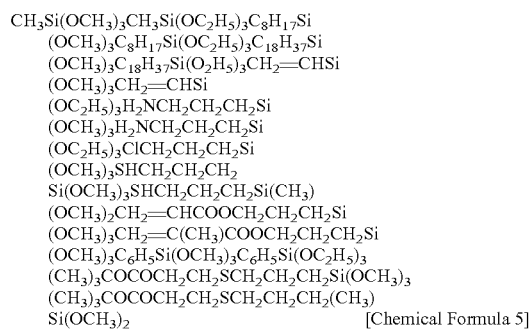

[Chemical Formula 6]

-continued

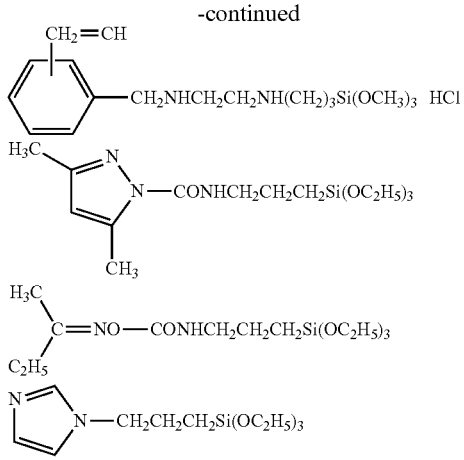

The addition amount of the silicon-based compound represented by the formula (2) is usually from 0.01 to 4.95 mmol, and preferably from 0.1 to 3.0 mmol per gram of the metal oxide sol, which is a starting material.

When the amount is in the above-described range, properties that the silicon-based compound has (for example, dispersing properties, adhesiveness onto a substrate and curing properties, etc.) can be further exhibited. In addition, molecules of the silicon-based compound represented by the formula (2) are not self-condensed, and the film formability also becomes good.

The temperature when the silicon-based compound represented by the formula (2) is added is not limited, but is preferably from normal temperature (about 20° C.) to the boiling point.

The reaction temperature is not also limited, but is preferably from normal temperature (about 20° C.) to the boiling point.

The reaction time is not also limited, but is preferably from 2 to 48 hours, and in particular preferably from 8 to 24 hours.

When the silicon-based compound represented by the formula (2) is stable against being oxidized, it is allowable to cause the metal oxide sol to react simultaneously with the silane coupling agent having a functional group chemically convertible to a sulfonic acid group and the silicon-based compound represented by the formula (2), and subsequently cause the peroxide to act on the reaction product to convert the functional group to the sulfonic acid group.

The modified metal oxide sol of the present invention may further contain a metal alkoxide and/or an oligomer thereof.

The metal alkoxide is represented by the following formula (3):

[wherein M is silicon, titanium or aluminum, R is an alkyl group, preferably a lower alkyl group having 1 to 8 carbon atoms, and more preferably a lower alkyl group having 1 to 4 carbon atoms, and m is 3 or 4].

Examples of R described above include a methyl group, an ethyl group, a propyl group, an isopropyl group, a butyl group, a pentyl group, and a hexyl group.

M is preferably silicon. Preferred are tetramethoxysilane wherein R is a methyl group; tetraethoxysilane wherein R is an ethyl group; and tetraisopropoxysilane wherein R is an isopropyl group. Examples of the oligomer of the metal alkoxide can include low condensates each obtained by partially hydrolyzing an alkoxysilane.

The above-described metal alkoxide and/or the oligomer thereof usually undergoes a condensation reaction with the silanol of the metal oxide sol.

In other words, the metal alkoxide and/or the oligomer thereof is added to a solution of the above-described modified metal oxide sol modified with the functional group represented by the formula (1) or a solution of the modified metal oxide sol to which the silicon-based compound represented by the formula (2) is further added, and then the alkoxide and/or the oligomer thereof is caused to undergo a condensation reaction with the silanol of the metal oxide sol, thereby making it possible to obtain the target.

The addition amount of the metal alkoxide and/or the oligomer thereof is usually from 0.01 to 4.95 mmol, and preferably from 0.1 to 3.0 mmol per gram of the metal oxide sol, which is a starting material.

When the amount is in the above-described range, properties that the silicon-based compound has (for example, dispersing properties, curing properties, etc.) can be further exhibited. In addition, molecules of the silicon-based compound represented by the formula (2) are not self-condensed, and the film formability also becomes good.

The temperature when the metal alkoxide and/or the oligomer thereof is added is not limited, but is preferably from normal temperature (about 20° C.) to the boiling point.

The reaction temperature is not also limited, but is preferably from normal temperature (about 20° C.) to the boiling point.

The reaction time is not also limited, but is preferably from 2 to 48 hours, and in particular preferably from 8 to 24 hours.

The modified metal oxide sol of the present invention may further contain a compound having plural functional groups selected from the group consisting of hydroxyl groups, amino groups, epoxy groups, carboxy groups, thiol groups, and blocked isocyanate groups.

Examples of the above-described compound include polyethylene glycol, polytetramethylene glycol, polyester-based diol, polycarbonate-based diol, polycaprolactone-based diol, bisphenol-A/epichlorohydrin resins, epoxy novolac resins, alicyclic epoxy resins, brominated epoxy resins, aliphatic epoxy resins, polyfunctional epoxy resins, polyethyleneimine, pentaerythritoltetrakis (3-mercaptobutyrate), 1,12-dodecanoic diacid, ε-caprolactam, methyl ethyl ketoxime, and isophorone diisocyanate, 4,4'-dicyclohexylmethane diisocyanate, hexamethylene diisocyanate and toluene diisocyanate each blocked with 3,5-dimethylpyrazole groups.

The modified metal oxide sol of the present invention may be used as a hydrophilizing agent.

The modified metal oxide sol of the present invention may be used as a hydrophilic coating composition.

The hydrophilic coating composition of the present invention may further contain a diluting solvent in order to improve the workabilities (such as handleability and coatability). The diluting solvent is not limited as far as the solvent is unreactive with the modified metal oxide sol of the present invention, and is a solvent wherein the sol is soluble and/or dispersible. Examples thereof include ether-based solvents (such as tetrahydrofuran and dioxane), alcohol-based solvents (such as methyl alcohol, ethyl alcohol, n-propyl alcohol, iso-propyl alcohol, and n-butyl alcohol), ketone-based solvents (such as acetone, methyl ethyl ketone, and methyl isobutyl ketone), aprotic solvents (such as N,N-dimethylformamide, N,N-dimethylacetoamide, N-methylpyrrolidone, and dimethylsulfoxide) and water.

When the composition contains the diluting solvent, the content of the diluting solvent is, for example, such an amount that the weight percentage of the modified metal oxide sol of the present invention is from 0.01 to 15% by weight (preferably from 0.05 to 10% by weight, and in particular preferably from 0.1 to 7.5% by weight) to the whole of the solvents.

The hydrophilic coating composition of the present invention may further contain a surfactant in order to improve the workabilities (such as wettability to a substrate). Examples of the surfactant include ordinary hydrocarbon-based surfactants and fluorine-based surfactants (anionic surfactants, cationic surfactants, nonionic surfactants, and amphoteric surfactants). Of these surfactants, fluorine-based surfactants are preferred, which produce an effect even by the addition of a small amount thereof.

Specific examples of the fluorine-based surfactants include FUTARGENTs (product name) manufactured by NEOS COMPANY LIMITED described below: FUTARGENT 100, FUTARGENT 100C, FUTARGENT 110, FUTARGENT 150, FUTARGENT 150CH, FUTARGENT A-K, FUTARGENT 501, FUTARGENT 250, FUTARGENT 251, FUTARGENT 222F, FUTARGENT 208G, FUTARGENT 300, FUTARGENT 310, and FUTARGENT 400SW.

The hydrophilic coating composition of the present invention may be applied for the hydrophilization of surfaces of substrates, sheets, films and fibers made of glass, plastic materials {such as polymethyl methacrylate, polyethylene terephthalate, polybutylene terephthalate, polyethylene naphthalate, ABS, polycarbonate, polystyrene, epoxy resins, unsaturated polyester, melamine resins, diallyl phthalate, polyimide, urethane resins, nylon, polyethylene, polypropylene, polyvinyl chloride, fluororesins (such as polytetrafluoroethylene resins, polychlorotrifluoroethylene resins, polyvinylidene fluoride resins, polyvinyl fluoride resins, perfluoroalkoxyfluororesins, tetrafluoroethylene/hexafluoropropylene copolymer resins, ethylene/tetrafluoroethylene copolymer resins, and ethylene/chlorotrifluoroethylene copolymer resins), polybutadiene, polyisoprene, SBR, nitrile rubber, EPM, EPDM, epichlorohydrin rubber, neoprene rubber, polysulfide, and butyl rubber}, metals (such as iron, aluminum, stainless steel, titanium, copper, brass, and any alloy thereof), cellulose, a cellulose derivative, cellulose analogues (such as chitin, chitosan, and porphyran), natural fibers (such as silk and cotton), or for other purposes.

If necessary, in order to improve the bondability to a substrate or the like, it is allowable to use a primer, or a surface activating treatment (manner for heightening the surface energy of the front surface of the substrate), such as corona discharge treatment.

Examples of a method for applying a coating liquid comprising the coating composition of the present invention include dip coating, spin coating, flow coating, and spray coating.

After the coating liquid is applied by any of the above-described coating methods or some other method, and then dried, the dried matter may be subjected to a treatment with a substance (catalyst, for example, a basic substance such as ammonia gas) and the like for promoting dehydration condensation for curing the produced coating film, thereby improving the coating film in mechanical properties and chemical properties.

Alternatively, the dried matter may be subjected to a heat treatment to advance dehydration condensation to cure the dried matter, thereby improving the coating film in mechanical properties and chemical properties.

Alternatively, the above-described two methods may be conducted.

When the silicon-based compound represented by the formula (2) has polymerizability other than radical polymerization, cation polymerization, and dehydration condensation based on ene/thiol reaction and the like, the applied liquid coat may be polymerized by heat or light and subsequently caused to undergo dehydration condensation. Alternatively, polymerization may be conducted simultaneously with dehydration condensation. Examples of the light include ultraviolet rays and visible rays.

Examples of the catalyst for the dehydration condensation include bases and acids.

Examples of the bases include inorganic bases (such as sodium hydroxide, potassium hydroxide, sodium acetate, lithium acetate, potassium acetate, and ammonia) and organic bases {triethanolamine, triethylamine, triethylenediamine, N,N-dimethylpiperadine, benzyldimethylamine, 2-(dimethylaminomethyl)phenol, and 2,4,6-tris(dimethylaminomethyl)phenol}.

Examples of the acids include inorganic acids (such as hydrochloric acid and sulfuric acid) and organic acids (such as acetic acid and trifluoroacetic acid).

Further, a compound that receives light or heat to generate a base or an acid may be used.

When the silicon-based compound represented by the formula (2) has polymerizability, an initiator that receives light or heat to generate a radical may be used.

Examples of the initiator by light include radical photoinitiators such as 1-hydroxy-cyclohexyl-phenyl-ketone (IRGACURE 184), 2-benzyl-2-dimethylamino-1-(4-morpholinophenyl)-butanone-1 (IRGACURE 369), a eutectic mixture (IRGACURE 500) of 1-hydroxy-cyclohexyl-phenyl-ketone (IRGACURE 184) and benzophenone, 2,2-dimethoxy-1,2-diphenylethan-1-one (IRGACURE 651), bis($\eta^5$-2,4-cyclopentadien-1-yl)-bis(2,6-difluoro-3-(1H-pyrrol-1-yl)-phenyl) titanium (IRGACURE 784), bis(2,4,6-trimethylbenzoyl)-phenylphosphine oxide (IRGACURE 819), 2-methyl-1[4-(methylthio)phenyl]-2-morpholinopropan-1-one (IRGACURE 907), 2-hydroxy-2-methyl-1-phenyl-propan-1-one (DAROCUR 1173), 1-[4-(2-hydroxyethoxy)-phenyl]-2-hydroxy-2-methyl-1-propan-1-one (IRGACURE 2959), a 1:4 liquid mixture (IRGACURE 1000) of 1-hydroxy-cyclohexyl-phenyl-ketone (IRGACURE 184) and 2-hydroxy-2-methyl-1-phenyl-propan-1-one (DAROCUR 1173), a 1:3 mixture (IRGACURE 1700) of bis(2,6-dimethoxybenzoyl)-2,4,4-trimethyl-pentylphosphine oxide and 2-hydroxy-2-methyl-1-phenyl-propan-1-one (DAROCUR 1173), a 1:3 mixture (IRGACURE 1800) of bis(2,6-dimethoxybenzoyl)-2,4,4-trimethyl-pentylphosphine oxide and 1-hydroxy-cyclohexyl-phenyl-ketone (IRGACURE 184), and a 1:1 mixture (IRGACURE 1850) of bis(2,6-dimethoxybenzoyl)-2,4,4-trimethyl-pentylphosphine oxide and 1-hydroxy-cyclohexyl-phenyl-ketone (IRGACURE 184); and cationic photoinitiators such as bis(4-tert-butylphenyl)iodonium hexafluorophosphate, bis(4-tert-butylphenyl)iodonium trifluoromethanesulfonate, diphenyliodonium hexafluoroarsenate, diphenyliodonium hexafluorophosphate, diphenyliodonium trifluoromethanesulfonate, 4-isopropyl-4'-methyldiphenyliodonium tetrakis(pentafluorophenyl)borate, triphenylsulfonium tetrafluoroborate, tri-p-tolylsulfonium hexafluorophosphate, and tri-p-tolylsulfonium trifluoromethanesulfonate.

Examples of the initiator by heat include azo-based initiators such as α,α'-azobisisobutyronitrile, 2,2'-azobis(4-methoxy-2,4-dimethylvaleronitrile), 2,2'-azobis(2,4 dimethylvaleronitrile), dimethyl 2,2'-azobis(2-methylpropionate), 2,2'-azobis(methylbutyronitrile, 1,1'-azobis(cyclohexane-1-carbonitrile), 2,2-azobis[N-(2-propenyl)-2-methylpropionamide], 1-[(1-cyano-1-methylethyl)azo]formamide, 2,2'-azobis(N-butyl-2-methylpropionamide), and 2,2'-azobis(N-cyclohexyl-2-methylpropionamide; and peroxide-based initiators such as tert-butylperoxy-2-ethyl hexanoate, tert-hexylperoxy-2-ethyl hexanoate, 1,1,3,3-tetramethylbutylperoxy-2-ethyl hexanoate, 2,5-dimethyl-2,5-di(2-ethylhexanoylperoxy)hexane, tert-butylperoxy pivalate, tert-hexylperoxy pivalate, tert-butylperoxy neodecanoate, benzoyl peroxide, dilauroyl peroxide, di(3,5,5-trimethylhexanoyl) peroxide, tert-butyl hydroperoxide, 1,1,3,3-tetramethylbutyl hydroperoxide, tert-butylcumyl peroxide, di-tert-hexyl peroxide, diisopropylperoxy dicarbonate, and di-2-ethylhexylperoxy dicarbonate.

These catalysts may be added to a coating liquid and then may be coated. Alternatively, after a film is formed, a solution into which any of the catalysts is dissolved may be sprayed thereon or the film may be exposed to a catalyst-containing atmosphere.

When the film is cured only by heat treatment, the heat treatment temperature is usually from 60 to 250° C., preferably from 80 to 225° C., and in particular preferably from 100 to 200° C.

The period when the heat treatment is conducted is usually from 0.05 to 48 hours, preferably from 0.1 to 48 hours, and in particular preferably from 0.5 to 36 hours.

When the dehydration condensation catalyst is used, the heat treatment temperature is from room temperature to the above-described temperature, and the heat treatment period is equal to the above-described period.

When the photoinitiator is used, the intensity of light to be radiated is usually from 100 to 3000 mJ, preferably from 500 to 2000 mJ, and in particular preferably from 750 to 2000 mJ.

When the thermal initiator is used, the heat treatment temperature is usually from 60 to 250° C., preferably from 80 to 225° C., and in particular preferably from 100 to 200° C.

A solid obtained by removing the solvent in the modified metal oxide sol of the present invention may be used as a resin-added type antistatic agent.

The solid is preferably a powder.

The solid can be obtained by removing a volatile component in the above-described modified metal oxide sol.

When the volatile component in the above-described modified metal oxide sol is removed, a different inorganic filler may be added thereto to remove the solvent, or the sol may be sprayed onto the inorganic filler to remove the solvent, thereby carrying the remnant thereon.

The inorganic filler is not particularly limited, and examples thereof include silica, alumina, titanium dioxide particles, inorganic whiskers, and glass fibers. Of these fillers, preferred are whiskers and glass fibers large in aspect ratio.

Examples of a method for removing the volatile component include a spray drying method, a freeze-drying method, and a natural drying (air drying) method.

The antistatic agent of the present invention may be used as a resin-added type antistatic agent, the resin including polycarbonate, polymethyl methacrylate, polyethylene terephthalate, polystyrene, ABS, polyamide, polyethylene, polypropylene, a polycarbonate/ABS alloy and the like.

The addition amount of the antistatic agent of the present invention to the resin is usually from 1 to 60% by weight, preferably from 1 to 30% by weight, and in particular preferably from 1 to 20% by weight.

A method for adding the antistatic agent to the resin may be a method of adding the powder directly thereto, followed by kneading, or a method of dispersing the powder in a solvent into which the resin is dissolved, and removing the solvent, or re-precipitating.

Alternatively, it is allowable to substitute a solvent into which the resin is dissolved for the solvent in a solution of the metal oxide sol of the present invention, dissolve the resin to mix the resin with the metal oxide sol, and then remove a volatile component to obtain the resin containing the antistatic agent.

The temperature in the case of the direct addition of the powder followed by kneading is usually from 120 to 300° C., and preferably from 150 to 300° C.

EXAMPLES

Hereinafter, the present invention will be specifically described by way of examples. The examples are not for restricting but for explaining the present invention. Hereinafter, the term "part(s)" denotes part(s) by weight unless otherwise specified.

Example 1

Into 39 parts of ethanol was dissolved 1.0 part (5.1 parts by mol) of 3-(trimethoxysilyl)propane-1-thiol (CHISSO CORPORATION), and then thereto were added 3.0 parts of an organosilica sol (30% solution in methanol, manufactured by Nissan Chemical Industries, Ltd.), 5.0 parts of water, and 2.9 parts (25.5 parts by mol) of hydrogen peroxide water (30% solution in water, manufactured by Santoku Chemical Industries Co., Ltd.). These components were heated and refluxed for 24 hours. After the end of the reaction, the reaction system was cooled to room temperature. Thereafter, 0.214 parts (5.1 parts by mol) of a lithium hydroxide monohydrate was dissolved in a slight amount of water, and this solution was added to the reaction system to neutralize the system, thereby obtaining a solution in ethanol containing the compound of the present invention, a methanol silica sol modified with $LiOSO_2$—$CH_2CH_2CH_2Si$(—O—)$_3$ groups.

Example 2

Into 36 parts of ethanol was dissolved 1.0 part (5.1 parts by mol) of 3-(trimethoxysilyl)propane-1-thiol (CHISSO CORPORATION), and then thereto were added 3.0 parts of an organosilica sol (30% solution in methanol, manufactured by Nissan Chemical Industries, Ltd.) and 10.0 parts of water. These components were heated and refluxed for 24 hours. After the reaction system was cooled, thereto was added 3.5 parts (30.8 parts by mol) of hydrogen peroxide water (30% solution in water, manufactured by Santoku Chemical Industries Co., Ltd.), and the components were heated and refluxed for 24 hours. After the end of the reaction, the reaction system was cooled to room temperature. Thereafter, 0.214 parts (5.1 parts by mol) of a lithium hydroxide monohydrate was dissolved in a slight amount of water, and this solution was added to the reaction system to neutralize the system, thereby obtaining a solution in ethanol containing the compound of the present invention, a methanol silica sol modified with $LiOSO_2$—$CH_2CH_2CH_2Si$(—O—)$_3$ groups.

Example 3

The same manner as in Example 2 was performed except that the amount of ethanol was changed from 36 parts to 34 parts, and that of the organosilica sol (30% solution in methanol, manufactured by Nissan Chemical Industries, Ltd.) was changed from 3.0 parts to 5.0 parts to obtain a solution in ethanol containing the compound of the present invention, a methanol silica sol modified with $LiOSO_2$—$CH_2CH_2CH_2Si$(—O—)$_3$ groups.

Example 4

The same manner as in Example 2 was performed except that the amount of ethanol was changed from 36 parts to 32 parts, and that of the organosilica sol (30% solution in methanol, manufactured by Nissan Chemical Industries, Ltd.) was changed from 3.0 parts to 7.0 parts to obtain a solution in ethanol containing the compound of the present invention, a methanol silica sol modified with $LiOSO_2$—$CH_2CH_2CH_2Si$(—O—)$_3$ groups.

Example 5

The same manner as in Example 2 was performed except that the amount of ethanol was changed from 36 parts to 32 parts, and that of the organosilica sol (30% solution in methanol, manufactured by Nissan Chemical Industries, Ltd.) was changed from 3.0 parts to 10.0 parts to obtain a solution in ethanol containing the compound of the present invention, a methanol silica sol modified with $LiOSO_2$—$CH_2CH_2CH_2Si$(—O—)$_3$ groups.

Example 6

The same manner as in Example 2 was performed except that the amount of ethanol was changed from 36 parts to 34 parts, that of the organosilica sol (30% solution in methanol, manufactured by Nissan Chemical Industries, Ltd.) was changed from 3.0 parts to 5.0 parts, and 0.214 parts (5.1 parts by mol) of the lithium hydroxide monohydrate was changed to 5.1 parts by volume (5.1 parts by mol) of a 1 N solution of sodium hydroxide in water (manufactured by Nacalai Tesque Inc.) to obtain a solution in ethanol containing the compound of the present invention, a methanol silica sol modified with $NaOSO_2$—$CH_2CH_2CH_2Si$(—O—)$_3$ groups.

Example 7

The same manner as in Example 2 was performed except that the amount of ethanol was changed from 36 parts to 34 parts, that of the organosilica sol (30% solution in methanol, manufactured by Nissan Chemical Industries, Ltd.) was changed from 3.0 parts to 5.0 parts, and 0.214 parts (5.1 parts by mol) of the lithium hydroxide monohydrate was changed to 5.1 parts by volume (5.1 parts by mol) of a 1 N solution of potassium hydroxide in water (manufactured by Nacalai Tesque Inc.) to obtain a solution in ethanol containing the compound of the present invention, a methanol silica sol modified with $KOSO_2$—$CH_2CH_2CH_2Si$(—O—)$_3$ groups.

Example 8

The same manner as in Example 2 was performed except that the amount of ethanol was changed from 36 parts to 34 parts, that of the organosilica sol (30% solution in methanol, manufactured by Nissan Chemical Industries, Ltd.) was changed from 3.0 parts to 5.0 parts, and 0.214 parts (5.1 parts by mol) of the lithium hydroxide monohydrate was changed to 0.289 parts (5.1 parts by mol) of ammonia (30% solution in water, manufactured by Nacalai Tesque Inc.) to obtain a solution in ethanol containing the compound of the present invention, a methanol silica sol modified with $NH_4OSO_2$-$CH_2CH_2CH_2Si$(—O—)$_3$ groups.

Example 9

The same manner as in Example 2 was performed except that the amount of ethanol was changed from 36 parts to 34 parts, that of the organosilica sol (30% solution in methanol, manufactured by Nissan Chemical Industries, Ltd.) was changed from 3.0 parts to 5.0 parts, and 0.214 parts (5.1 parts by mol) of the lithium hydroxide monohydrate was changed to 0.515 parts (5.1 parts by mol) of tetraethylammonium hydroxide (manufactured by Nacalai Tesque Inc.) to obtain a solution in ethanol containing the compound of the present invention, a methanol silica sol modified with $N(C_2H_5)_4OSO_2$—$CH_2CH_2CH_2Si$(—O—)$_3$ groups.

Example 10

Into 34 parts of ethanol was dissolved 1.0 part (5.1 parts by mol) of 3-(trimethoxysilyl)propane-1-thiol (CHISSO CORPORATION), and then thereto were added 5.0 parts of an organosilica sol (30% solution in methanol, manufactured by Nissan Chemical Industries, Ltd.) and 10.0 parts of water. These components were heated and refluxed for 24 hours. After the reaction system was cooled, thereto was added 3.5 parts (30.8 parts by mol) of hydrogen peroxide water (30% solution in water, manufactured by Santoku Chemical Industries Co., Ltd.), and these components were heated and refluxed for 24 hours, thereby obtaining a solution in ethanol containing the compound of the present invention, a methanol silica sol modified with $HOSO_2$—$CH_2CH_2CH_2Si$(—O—)$_3$ groups.

Example 11

The same manner as in Example 2 was performed except that the amount of ethanol was changed from 36 parts to 24 parts, and that of the organosilica sol (30% solution in methanol, manufactured by Nissan Chemical Industries, Ltd.) was changed from 3.0 parts to 15.0 parts to obtain a solution in ethanol containing the compound of the present invention, a methanol silica sol modified with $LiOSO_2$—$CH_2CH_2CH_2Si$(—O—)$_3$ groups.

Example 12

The same manner as in Example 3 was performed except that ethanol was changed to methanol to obtain a solution in methanol containing the compound of the present invention, a methanol silica sol modified with $LiOSO_2$—$CH_2CH_2CH_2Si$(—O—)$_3$ groups.

Example 13

The same manner as in Example 11 was performed except that ethanol was changed to methanol to obtain a solution in methanol containing the compound of the present invention, a methanol silica sol modified with $LiOSO_2$—$CH_2CH_2CH_2Si$(—O—)$_3$ groups.

Example 14

The same manner as in Example 2 was performed except that the amount of ethanol was changed from 36 parts to 24 parts, 3.0 parts of the organosilica sol (30% solution in methanol, manufactured by Nissan Chemical Industries, Ltd.) was changed to 5.0 parts of a silica sol (30% ST sol in isopropanol, manufactured by Nissan Chemical Industries, Ltd.), and 0.214 parts (5.1 parts by mol) of the lithium hydroxide monohydrate was changed to 0.591 parts (25.5 parts by mol) of silver oxide to obtain a solution in ethanol containing the compound of the present invention, an isopropanol silica sol modified with $AgOSO_2$—$CH_2CH_2CH_2Si$(—O—)$_3$ groups.

Example 15

(1) Into 375 parts of ethanol was dissolved 15.0 parts (76.5 parts by mol) of 3-(trimethoxysilyl)propane-1-thiol (CHISSO CORPORATION), and then thereto were added 90.0 parts of an organosilica sol (30% solution in isopropanol, IPA-ST, manufactured by Nissan Chemical Industries, Ltd.) and 100.0 parts of water. These components were heated and refluxed for 24 hours. After the reaction system was cooled, thereto was added 52.5 parts (463 parts by mol) of hydrogen peroxide water (30% solution in water, manufactured by Santoku Chemical Industries Co., Ltd.), and the components were heated and refluxed for 24 hours. After the end of the reaction, the reaction system was cooled to room temperature. Thereafter, 3.21 parts (76.5 parts by mol) of a lithium hydroxide monohydrate was dissolved in 15 parts of water, and this solution was added to the reaction system to neutralize the system. Water was further added thereto to adjust the total amount to 750 parts, thereby obtaining 750 parts of a solution in ethanol containing the compound of the present invention, an isopropanol silica sol modified with $LiOSO_2$—$CH_2CH_2CH_2Si$(—O—)$_3$ groups.

(2) Into 100 mL of dehydrated ethyl acetate were dissolved 4.81 parts (50.0 parts by mol) of 3,5-dimethylpyrazole and 12.35 parts (50.0 parts by mol) of 3-isocyanatopropyltriethoxysilane, and the solution was stirred at room temperature for 3 days. After the end of the reaction, ethyl acetate was removed to obtain 16.8 parts of a blocked isocyanate compound wherein the isocyanate groups of 3-isocyanatopropyltriethoxysilane were blocked with 3,5-dimethylpyrazole.

(3) To 49 parts of the solution in ethanol, obtained in (1), containing an isopropanol silica sol modified with $LiOSO_2$—$CH_2CH_2CH_2Si$(—O—)$_3$ groups was added 1.0 g of the blocked isocyanate compound obtained in (2), and the resultant was stirred at room temperature for 3 days to obtain 50 parts of a solution in ethanol containing an isopropanol silica sol modified with $LiOSO_2$—$CH_2CH_2CH_2Si$(—O—)$_3$ groups and blocked isocyanate groups.

Example 16

To 49.0 parts of the solution in ethanol, obtained in (1) in Example 15, containing an isopropanol silica sol modified with $LiOSO_2$—$CH_2CH_2CH_2Si$(—O—)$_3$ groups was added 1.0 part of tetraethoxysilane, and the resultant was stirred at room temperature for 3 days to obtain 50 parts of a solution in ethanol containing a sol wherein a hydrolyzate of tetraethoxysilane was condensed with the isopropanol silica sol modified with $LiOSO_2$—$CH_2CH_2CH_2Si$(—O—)$_3$ groups.

Example 17

To 49.0 parts of the isopropanol silica sol, obtained in (3) in Example 15, modified with $LiOSO_2$—$CH_2CH_2CH_2Si$(—O—)$_3$ groups and blocked isocyanate groups was added 1.0 part of tetraethoxysilane, and the resultant was stirred at room temperature for 3 days to obtain 50 parts of a solution in ethanol containing a sol wherein a hydrolyzate of tetraethoxysilane was condensed with the isopropanol silica sol modified with $LiOSO_2$—$CH_2CH_2CH_2Si$(—O—)$_3$ groups and blocked isocyanate groups.

Example 18

To 49.0 parts of the solution in ethanol, obtained in (1) in Example 15, containing an isopropanol silica sol modified with $LiOSO_2$—$CH_2CH_2CH_2Si$(—O—)$_3$ groups was added 2.5 parts of a tetraethoxysilane oligomer (40% solution in ethanol, ETHYL SILICATE 40, manufactured by COLCOAT CO., LTD.), and the resultant was stirred at room temperature for 3 days to obtain 51.5 parts of a solution in ethanol containing a sol wherein a hydrolyzate of tetraethoxysilane was condensed with the isopropanol silica sol modified with $LiOSO_2$—$CH_2CH_2CH_2Si$(—O—)$_3$ groups.

Example 19

To 49.0 parts of the isopropanol silica sol, obtained in (3) in Example 15, modified with $LiOSO_2$—$CH_2CH_2CH_2Si$(—O—)$_3$ groups and blocked isocyanate groups was added 2.5 parts of a tetraethoxysilane oligomer (40% solution in ethanol, ETHYL SILICATE 40, manufactured by COLCOAT CO., LTD.), and the resultant was stirred at room temperature for 3 days to obtain 51.5 parts of a solution in ethanol containing a sol wherein the tetraethoxysilane oligomer was condensed with the isopropanol silica sol modified with $LiOSO_2$—$CH_2CH_2CH_2Si$(—O—)$_3$ groups and blocked isocyanate groups.

Example 20

(1) To 49 parts of the solution in ethanol, obtained in (1) in Example 15, containing an isopropanol silica sol modified with $LiOSO_2$—$CH_2CH_2CH_2Si$(—O—)$_3$ groups was added 1.0 part of 3-(trimethoxysilyl)propane-1-thiol (CHISSO CORPORATION), and the resultant was stirred at room temperature for 3 days to obtain 50 parts of a solution in ethanol containing an isopropanol silica sol modified with $LiOSO_2$—$CH_2CH_2CH_2Si$(—O—)$_3$ groups and thiol groups.

(2) To 49 parts of the solution in ethanol, obtained in (1) in Example 15, containing an isopropanol silica sol modified with $LiOSO_2$—$CH_2CH_2CH_2Si$(—O—)$_3$ groups was added 1.0 part of γ-glycidoxypropyltriethoxysilane (CHISSO CORPORATION), and the resultant was stirred at room temperature for 3 days to obtain 50 parts of a solution in ethanol containing an isopropanol silica sol modified with $LiOSO_2$—$CH_2CH_2CH_2Si$(—O—)$_3$ groups and glycidoxy groups.

(3) Fifteen parts of the solution in ethanol, obtained in (1) described above, containing an isopropanol silica sol modified with $LiOSO_2$—$CH_2CH_2CH_2Si$(—O—)$_3$ groups and thiol groups, and 15 parts of the solution in ethanol, obtained in (2) described above, containing an isopropanol silica sol modified with $LiOSO_2$—$CH_2CH_2CH_2Si$(—O—)$_3$ groups and glycidoxy groups were diluted with 30 parts of ethanol to obtain 50 parts of a mixed solution.

Example 21

Fifteen parts of the solution in ethanol, obtained in (3) in Example 15, containing an isopropanol silica sol modified with $LiOSO_2$—$CH_2CH_2CH_2Si$(—O—)$_3$ groups and blocked isocyanate groups, 15 parts of the solution in ethanol, obtained in (1) in Example 20, containing an isopropanol silica sol modified with $LiOSO_2$—$CH_2CH_2CH_2Si$(—O—)$_3$ groups and thiol groups, and 15 parts of the solution in ethanol, obtained in (2) in Example 20, containing an isopropanol silica sol modified with $LiOSO_2$—$CH_2CH_2CH_2Si$(—O—)$_3$ groups and glycidoxy groups were mixed with one another to obtain 45 parts of a mixed solution.

Example 22

Twelve parts of the solution in ethanol, obtained in (3) in Example 15, containing an isopropanol silica sol modified with $LiOSO_2$—$CH_2CH_2CH_2Si$(—O—)$_3$ groups and blocked isocyanate groups, 12 parts of the solution in ethanol, obtained in (2) in Example 20, containing an isopropanol silica sol modified with $LiOSO_2$—$CH_2CH_2CH_2Si$(—O—)$_3$ groups and glycidoxy groups, and 24 parts of ethanol were mixed with one another to obtain 48 parts of a mixed solution.

Example 23

Twelve parts of the solution in ethanol, obtained in (3) in Example 15, containing an isopropanol silica sol modified with LiOSO$_2$—CH$_2$CH$_2$CH$_2$Si(—O—)$_3$ groups and blocked isocyanate groups, 12 parts of the solution in ethanol, obtained in (1) in Example 20, containing an isopropanol silica sol modified with LiOSO$_2$—CH$_2$CH$_2$CH$_2$Si(—O—)$_3$ groups and thiol groups, and 24 parts of ethanol were mixed with one another to obtain 48 parts of a mixed solution.

Example 24

To 24 parts of the solution in ethanol, obtained in (1) in Example 15, containing an isopropanol silica sol modified with LiOSO$_2$—CH$_2$CH$_2$CH$_2$Si(—O—)$_3$ groups were added 0.5 parts of 3-(trimethoxysilyl)propane-1-thiol (CHISSO CORPORATION) and 0.5 parts of γ-glycidoxypropyltriethoxysilane (CHISSO CORPORATION). The resultant was stirred at room temperature for 3 days, and then 25 parts of ethanol were mixed therewith to obtain 50 parts of a solution in ethanol containing an isopropanol silica sol modified with LiOSO$_2$—CH$_2$CH$_2$CH$_2$Si(—O—)$_3$ groups, thiol groups, and glycidoxy groups.

Example 25

(1) Into 270 parts of dehydrated ethyl acetate were dissolved 19.6 parts of 3-(trimethoxysilyl)propane-1-thiol (CHISSO CORPORATION) and 12.8 parts of tert-butyl acrylate (manufactured by Tokyo Chemical Industry Co., Ltd.). Using 0.328 parts of azobisisobutyronitrile (AIBN) as a catalyst, these components were heated and refluxed under an argon atmosphere for 24 hours. After the end of the reaction, ethyl acetate was removed to obtain 30.1 parts of a silane coupling agent modified with tert-butyl ester.

(2) At room temperature, 1.0 part of the silane coupling agent obtained in (1) described above and 49 parts of the solution in ethanol, obtained in (1) in Example 15, containing an isopropanol silica sol modified with LiOSO$_2$—CH$_2$CH$_2$CH$_2$Si(—O—)$_3$ groups were stirred for 3 days to obtain 50 parts of a solution in ethanol containing an isopropanol silica sol modified with LiOSO$_2$—CH$_2$CH$_2$CH$_2$Si(—O—)$_3$ groups and tert-butyl ester.

(3) Fifteen parts of the solution in ethanol, obtained in (2) described above, containing an isopropanol silica sol modified with LiOSO$_2$—CH$_2$CH$_2$CH$_2$Si(—O—)$_3$ groups and tert-butyl ester, 15 parts of the solution in ethanol, obtained in (2) in Example 20, containing an isopropanol silica sol modified with LiOSO$_2$—CH$_2$CH$_2$CH$_2$Si(—O—)$_3$ groups and glycidoxy groups were diluted with 30 parts of ethanol to obtain 50 parts of a mixed solution.

Hydrophilicity Evaluation Results 1

The modified metal oxide sol obtained in each of Examples 1 to 14 was diluted 25 times with ethanol (a mixed liquid of ethanol and water if necessary) to prepare a treating liquid (surface hydrophilizing agent). A surface of a predetermined substrate was modified therewith, as will be described below. The contact angel thereof was measured. The results are shown in Table 1.

(1) Microscope slides {76 mm, 26 mm, 1.2 mm; microscope slides each prepared by immersing a glass piece in a saturated solution of sodium hydroxide in 2-propanol, washing the piece with water and drying the piece (at 60° C. for 2 hours)} were immersed in the treating liquid (surface hydrophilizing agent), and then taken out. Thereafter, the liquid was removed therefrom. One of the microscope slides was subjected to a heating treatment at 120° C. for 24 hours, and the other thereof was subjected to an ammonia gas treatment at room temperature for 10 minutes. In this way, surface-modified microscope slides of two types were obtained.

(2) A polycarbonate plate {76 mm, 26 mm, 1.0 mm; plate prepared by immersing an original polycarbonate plate in a highly adhesive silica primer (manufactured by JAPAN NANO COAT CO., LTD.), taking out the polycarbonate plate, removing the liquid therefrom, and being subjected to a heating treatment at 100° C. for 1 hour} was immersed in the treating liquid (surface hydrophilizing agent), and then taken out. Thereafter, the liquid was removed therefrom. This plate was subjected to a heating treatment at 100° C. for 24 hours to obtain a surface-modified polycarbonate plate.

A contact angle measuring device {DROP MASTER 500, Kyowa Interface Science Co., Ltd.; droplet amount: 2 μL, measurement interval: 1000 ms, and the number of times of measurement: 30} was used to measure the contact angle (degrees) of any five points on the front surface of a surface-modified microscope slide. An average value was then calculated.

TABLE 1

| Treating liquid | Substrate | Contact agent (°) |
| --- | --- | --- |
| Example 1 | Microscope slide | 9.7 |
| Example 2 | Microscope slide | 4.6 |
| Example 3 | Microscope slide | 2.7 |
| Example 3 | Ammonia gas-treated, microscope slide | 4.7 |
| Example 4 | Microscope slide | 2.6 |
| Example 4 | Ammonia gas-treated, microscope slide | 6.7 |
| Example 5 | Microscope slide | 3.3 |
| Example 6 | Microscope slide | 7.3 |
| Example 7 | Microscope slide | 6.5 |
| Example 8 | Microscope slide | 8.6 |
| Example 9 | Microscope slide | 3.8 |
| Example 10 | Microscope slide | 2.5 |
| Example 11 | Microscope slide | 4.0 |
| Example 12 | Microscope slide | 3.1 |
| Example 13 | Microscope slide | 3.8 |
| Example 13 | Ammonia gas-treated, microscope slide | 3.9 |
| Example 13 | Polycarbonate | 4.5 |
| Example 14 | Microscope slide | 4.5 |
| Example 14 | Ammonia gas-treated, microscope slide | 6.8 |
| None | Microscope slide | 46.2 |
| None | Polycarbonate | 93.3 |

Hydrophilicity Evaluation Results 2

The modified metal oxide sol obtained in each of Examples 15 to 25 was diluted predetermined times with ethanol (a mixed liquid of ethanol and water if necessary) to prepare a treating liquid (surface hydrophilizing agent). A surface of a predetermined substrate was modified therewith, as will be described below. The contact angel thereof was measured. The results are shown in Table 2.

A polymethyl methacrylate plate (76 mm×26 mm, thickness: 1.0 mm), a polycarbonate plate (76 mm×26 mm, thickness: 1.0 mm), a polyethylene terephthalate sheet (76 mm×26 mm, thickness: 100 μm), a polyester sheet (a product wherein a steel plate was coated with a polyester; 76 mm×26 mm, thickness: unclear), a polyurethane sheet (76 mm×26 mm, thickness: 100 μm), an unsaturated polyester resin plate (76 m×26 mm, thickness: 5.0 mm), an aluminum plate (76 mm×26 mm, thickness: 1.0 mm), a stainless steel plate (76 mm×26 mm, thickness: 1.0 mm), and the like were washed with ethanol, and dried. The plates or the sheets were immersed in the treating liquid (surface hydrophilizing agent), and then taken out. Thereafter, the liquid was removed therefrom, and the plates or the sheets were subjected to a heating treatment at a predetermined temperature for a predetermined period to obtain surface-modified plates or sheets.

TABLE 2

| Treating liquid | Substrate | Contact agent (°) |
|---|---|---|
| Example 15 | Polymethyl methacrylate plate (diluted 5 times), 80° C., 24 hours | 47.8 |
| Example 15 | Polycarbonate plate (diluted 5 times), 130° C., 24 hours | 33.0 |
| Example 15 | Polyurethane sheet (diluted 5 times), 130° C., 30 minutes | 35.0 |
| Example 15 | Polyethylene terephthalate sheet (diluted 5 times), 130° C., 24 hours | 63.6 |
| Example 15 | Polyester sheet (diluted 5 times), 130° C., 24 hours | 19.8 |
| Example 15 | Unsaturated polyester resin plate (diluted 5 times), 130° C., 24 hours | 7.1 |
| Example 15 | Stainless steel plate (not diluted), 200° C., 30 minutes | 37.9 |
| Example 15 | Aluminum plate (not diluted), 200° C., 30 minutes | 43.8 |
| Example 15 | Copper plate (not diluted), 200° C., 30 minutes | 69.8 |
| Example 15 | Brass plate (not diluted), 200° C., 30 minutes | 15.0 |
| Example 16 | Microscope slide (diluted 20 times), room temperature, 24 hours | 23.5 |
| Example 17 | Polycarbonate plate (diluted 5 times), 130° C., 24 hours | 17.1 |
| Example 18 | Microscope slide (diluted 20 times), room temperature, 24 hours | 20.5 |
| Example 19 | Polycarbonate plate (diluted 5 times), 130° C., 24 hours | 28.5 |
| Example 20 | Polycarbonate plate (not diluted), 130° C., 24 hours | 24.8 |
| Example 20 | Polymethyl methacrylate plate (not diluted), 80° C., 24 hours | 22.9 |
| Example 21 | Polycarbonate plate (diluted 4 times), 130° C., 24 hours | 34.7 |
| Example 22 | Polycarbonate plate (not diluted), 130° C., 24 hours | 28.7 |
| Example 23 | Polycarbonate plate (not diluted), 130° C., 24 hours | 17.1 |
| Example 24 | Polycarbonate plate (not diluted), 130° C., 24 hours | 20.3 |
| Example 25 | Polycarbonate plate (not diluted), 130° C., 24 hours | 16.0 |
| None | Polymethyl methacrylate plate | 72.1 |
| None | Polyurethane sheet | 90.5 |
| None | Polyethylene terephthalate sheet | 80.9 |
| None | Polyester sheet | 84.3 |
| None | Unsaturated polyester resin plate | 80.0 |
| None | Stainless steel plate | 88.5 |
| None | Aluminum plate | 93.6 |
| None | Copper plate | 89.9 |
| None | Brass plate | 97.1 |

As is evident from Tables 1 and 2, the hydrophilizing agent of the present invention is remarkably smaller in contact angle than the untreated product. Thus, it is understood that the hydrophilizing agent of the present invention is excellent in hydrophilizing effect.

Example 26

(1) To 49 parts of the solution in ethanol, obtained in (1) in Example 15, containing an isopropanol silica sol modified with $LiOSO_2$—$CH_2CH_2CH_2Si(—O—)_3$ groups was added 1.0 part of vinyltrimethoxysilane, and the resultant was stirred at room temperature for 3 days to obtain 50 parts of a solution in ethanol containing an isopropanol silica sol modified with $LiOSO_2$—$CH_2CH_2CH_2Si(—O—)_3$ groups and vinyl groups.

(2) To 49 parts of the solution in ethanol, obtained in (1) in Example 15, containing an isopropanol silica sol modified with $LiOSO_2$—$CH_2CH_2CH_2Si(—O—)_3$ groups was added 1.0 part of 3-(trimethoxysilyl)propane-1-thiol (CHISSO CORPORATION), and the resultant was stirred at room temperature for 3 days to obtain 50 parts of a solution in ethanol containing an isopropanol silica sol modified with $LiOSO_2$—$CH_2CH_2CH_2Si(—O—)_3$ groups and thiol groups.

(3) Fifteen parts of the solution in ethanol, obtained in (1) described above, containing an isopropanol silica sol modified with $LiOSO_2$—$CH_2CH_2CH_2Si(—O—)_3$ groups and vinyl groups, and 15 parts of the solution in ethanol, obtained in (2) described above, containing an isopropanol silica sol modified with $LiOSO_2$—$CH_2CH_2CH_2Si(—O—)_3$ groups and thiol groups were diluted with 25 parts of ethanol. Thereto were added 0.06 parts of IRGACURE 184 and 0.025 parts of FUTARGENT 251 as photoinitiators to obtain a photosensitive hydrophilic coating liquid.

Example 27

(1) To 49 parts of the solution in ethanol, obtained in (1) in Example 15, containing an isopropanol silica sol modified with $LiOSO_2$—$CH_2CH_2CH_2Si(—O—)_3$ groups was added 1.0 part of 3-methacryloxypropyltrimethoxysilane (CHISSO CORPORATION), and the resultant was stirred at room temperature for 3 days to obtain 50 parts of a solution in ethanol containing an isopropanol silica sol modified with $LiOSO_2$—$CH_2CH_2CH_2Si(—O—)_3$ groups and methacrylic groups.

(2) Twenty-five parts of the solution in ethanol, obtained in (1), containing an isopropanol silica sol modified with $LiOSO_2$—$CH_2CH_2CH_2Si(—O—)_3$ groups and methacrylic groups was diluted with 25 parts of ethanol. Thereto were added 0.05 parts of IRGACURE 184 and 0.025 parts of FUTARGENT 251 as photoinitiators to obtain a photosensitive hydrophilic coating liquid.

Example 28

Ten parts of the solution in ethanol, obtained in (1) in Example 27, containing an isopropanol silica sol modified with $LiOSO_2$—$CH_2CH_2CH_2Si(—O—)_3$ groups and methacrylic groups, and 10 parts of the solution in ethanol, obtained in (1) in Example 20, containing an isopropanol silica sol modified with $LiOSO_2\text{—}CH_2CH_2CH_2Si(\text{—}O\text{—})_3$ groups and thiol groups were diluted with 10 parts of ethanol. Thereto were added 0.04 parts of IRGACURE 184 and 0.015 parts of FUTARGENT 251 as photoinitiators to obtain a photosensitive hydrophilic coating liquid.

Example 29

As photoinitiators, 0.056 parts of IRGACURE 184 was added to 14 parts of the solution in ethanol, obtained in (3) in Example 15, containing an isopropanol silica sol modified with $LiOSO_2\text{—}CH_2CH_2CH_2Si(\text{—}O\text{—})_3$ groups and blocked isocyanate groups, 14 parts of the solution in ethanol, obtained in (1) in Example 25, containing an isopropanol silica sol modified with $LiOSO_2\text{—}CH_2CH_2CH_2Si(\text{—}O\text{—})_3$ groups and vinyl groups, and 14 parts of the solution in ethanol, obtained in (2) in Example 16, containing an isopropanol silica sol modified with $LiOSO_2\text{—}CH_2CH_2CH_2Si(\text{—}O\text{—})_3$ groups and thiol groups to obtain a photosensitive hydrophilic coating liquid.

Example 30

Twenty-five parts of the solution in ethanol, obtained in (2) in Example 20, containing an isopropanol silica sol modified with $LiOSO_2\text{—}CH_2CH_2CH_2Si(\text{—}O\text{—})_3$ groups and glycidoxy groups was diluted with 25 parts of ethanol. Thereto was added 0.025 parts of diphenyliodonium hexafluorophosphate as a photoacid generator to obtain a photosensitive hydrophilic coating liquid.

Hydrophilicity Evaluation Results 3

The photosensitive hydrophilic coating liquid obtained in each of Examples 25 to 30 was diluted predetermined times with ethanol (a mixed liquid of ethanol and water if necessary) to prepare a treating liquid. A surface of a predetermined substrate was modified therewith, as will be described below. The contact angel thereof was measured. The results are shown in Table 3.

A polymethyl methacrylate plate (76 mm×26 mm, thickness: 1.0 mm), a polycarbonate plate (76 mm×26 mm, thickness: 1.0 mm), a polyethylene terephthalate sheet (76 mm×26 mm, thickness: 100 μm), and the like were washed with ethanol, and dried. The plates or the sheets were immersed in the treating liquid, and then taken out. Thereafter, he liquid was removed therefrom, and the plates or the sheets were irradiated with ultraviolet rays (apparatus: a light source apparatus for ultraviolet-curing, ECS-151U, manufactured by Eye Graphics Co., Ltd.; radiation amount: 1000 mJ), and then subjected to a heating treatment at a predetermined temperature for a predetermined period to obtain surface-modified plates.

TABLE 3

| Treating liquid | Substrate | Contact agent (°) |
| --- | --- | --- |
| Example 26 | Polymethyl methacrylate (not diluted), 80° C., 24 hours | 54.8 |
| Example 26 | Polycarbonate (not diluted), 130° C., 24 hours | 66.2 |
| Example 26 | Polyethylene terephthalate (not diluted), 130° C., 24 hours | 65.9 |
| Example 27 | Polymethyl methacrylate (not diluted), 80° C., 24 hours | 56.9 |
| Example 27 | Polycarbonate (not diluted), 130° C., 24 hours | 47.2 |
| Example 27 | Polyethylene terephthalate (not diluted), 130° C., 24 hours | 59.8 |
| Example 28 | Polymethyl methacrylate (not diluted), 80° C., 24 hours | 24.7 |
| Example 28 | Polycarbonate (not diluted), 130° C., 24 hours | 20.9 |
| Example 28 | Polyethylene terephthalate (not diluted), 130° C., 24 hours | 41.4 |
| Example 29 | Polymethyl methacrylate (not diluted), 80° C., 24 hours | 34.0 |
| Example 29 | Polycarbonate (not diluted), 130° C., 24 hours | 28.4 |
| Example 29 | Polyethylene terephthalate (not diluted), 130° C., 24 hours | 38.9 |
| Example 30 | Polymethyl methacrylate (not diluted), 80° C., 24 hours | 27.7 |

Example 31

Into 250 parts of ethanol were dissolved 7.84 parts (40.0 parts by mol) of 3-(trimethoxysilyl)propane-1-thiol (CHISSO CORPORATION) and 7.42 parts (40.0 parts by mol) of phenyltrimethoxysilane (manufactured by Tokyo Chemical Industry Co., Ltd.), and then thereto were added 50.0 parts of an organosilica sol (30% solution in isopropanol, IPA-ST, manufactured by Nissan Chemical Industries, Ltd.) and 65.0 parts of water. These components were heated and refluxed for 24 hours. After the reaction system was cooled, thereto was added 28.0 parts (247 parts by mol) of hydrogen peroxide water (30% solution in water, manufactured by Santoku Chemical Industries Co., Ltd.), and the components were heated and refluxed for 24 hours. After the end of the reaction, the reaction system was cooled to room temperature. Thereafter, 1.67 parts (40.0 parts by mol) of a lithium hydroxide monohydrate was dissolved in 15 g of water, and this solution was added to the reaction system to neutralize the system. The resultant solution was dried at room temperature, and the resultant solid was pulverized in a mortar to obtain 25 parts of a white powder (antistatic agent).

Example 32

Into 150 parts of ethanol were dissolved 10.0 parts (51.0 parts by mol) of 3-(trimethoxysilyl)propane-1-thiol (CHISSO CORPORATION) and 5.94 parts (30.0 parts by mol) of phenyltrimethoxysilane (manufactured by Tokyo Chemical Industry Co., Ltd.), and then thereto were added 100.0 parts of an organosilica sol (15% solution in isopropanol, IPA-ST-UP, manufactured by Nissan Chemical Industries, Ltd.) and 65.0 parts of water. These components were heated and refluxed for 24 hours. After the reaction system was cooled, thereto was added 35.0 parts (247 parts by mol) of hydrogen peroxide water (30% solution in water, manufactured by Santoku Chemical Industries Co., Ltd.), and the components were heated and refluxed for 24 hours. After the end of the reaction, the reaction system was cooled to room temperature. Thereafter, 2.14 parts (51.0 parts by mol) of a lithium hydroxide monohydrate was dissolved in 15 g of water, and this solution was added to the reaction system to neutralize the system. Two hundred parts of the resultant solution were dried at room temperature, and the resultant solid was pulverized in a mortar to obtain 17 parts of a white powder (antistatic agent).

Example 33

To 50 parts of the solution in ethanol, obtained in (1) in Example 15, containing an isopropanol silica sol modified with $LiOSO_2$—$CH_2CH_2CH_2Si$(—O—)$_3$ groups was added 100 parts of a pulverized product of glass fiber (milled fiber EFDE90-01, manufactured by Central Glass Co., Ltd.). The solvent was then removed therefrom, and the resultant was subjected to a heat treatment at 150° C. for 1 hour to obtain a conductive glass fiber.

Example 34

To 50 parts of the solution obtained in Example 33 was added 100 parts of a pulverized product of glass fiber (milled fiber EFDE90-01, manufactured by Central Glass Co., Ltd.). The solvent was then removed therefrom, and the resultant was subjected to a heat treatment at 150° C. for 1 hour to obtain a conductive glass fiber.

Antistatic Performance Evaluation Results (1)

The white powder (antistatic agent) obtained in each of Examples 31 and 32 was added to toluene wherein a polycarbonate (PCZ-400, manufactured by Mitsubishi Gas Chemical Company, Inc.) was dissolved at a concentration of 10% by weight so that the white powder had a predetermined concentration. A homogenizer (CLM2.2S, manufactured by MTEC Co., Ltd.) was used to stir the powder under an intense shear. In this way, a liquid dispersion was prepared. Next, the liquid dispersion was made into a sheet form through a casting method to obtain a transparent polycarbonate/antistatic agent composite sheet. A surface resistance meter (HIRESTA UP MCP-HT450, manufactured by Mitsubishi Chemical Corporation) was used to measure the surface resistance of the resultant sheet. The surface resistance value of the resultant sheet is shown in Table 4.

Antistatic Performance Evaluation Results (2)

The conductive glass fiber obtained in each of Examples 33 and 34 was melted and kneaded in a Laboplast mill (4M150, manufactured by Toyo Seiki Co., Ltd.) at 260° C. for 5 minutes so that the glass fiber had a predetermined concentration. The resultant compound was pressed at 260° C. and 0.5 MPa for 1 minute by a vacuum hot press (manufactured by TOSHIN CO., LTD.) to obtain a sheet of 0.5 mm thickness. The surface resistance value of the resultant sheet is shown in Table 4.

TABLE 4

| Antistatic agent (parts) | Polycarbonate (parts) | Surface resistance value [Ω] |
|---|---|---|
| Example 31 (20) | 80 | $3.1 \times 10^{12}$ |
| Example 32 (30) | 70 | $5.6 \times 10^{12}$ |
| Example 32 (50) | 50 | $3.5 \times 10^{9}$ |
| Example 33 (10) | 90 | $2.6 \times 10^{12}$ |
| Example 33 (20) | 80 | $3.5 \times 10^{11}$ |
| Example 33 (30) | 70 | $6.2 \times 10^{9}$ |
| Example 34 (10) | 90 | $2.5 \times 10^{11}$ |
| Example 34 (20) | 80 | $5.4 \times 10^{10}$ |
| Example 34 (30) | 70 | $1.7 \times 10^{9}$ |
| None | 100 | $10^{14}$ or more |

As is evident from the above-described results, in any system to which the modified metal oxide sol of the present invention is not added, the surface resistance value is $10^{13}$ Ω or more (measuring limit), which is very large, while in any system to which the modified metal oxide sol of the present invention is added, the surface resistance is lowered. Thus, it is understood that antistatic performance ($10^9$ to $10^{13}$ Ω) is given thereto.

INDUSTRIAL APPLICABILITY

The modified metal oxide sol of the present invention is large in hydrophilizing effect and antistatic effect, and is capable of being coating and can be produced at low costs. Thus, the sol is favorable for a hydrophilizing agent, an antistatic agent, a hydrophilic coating composition, an antibacterial agent, an electroconductive coating agent or an ion (proton) conductive coating agent.

The invention claimed is:

1. A modified metal oxide sol, wherein a metal oxide sol is chemically modified with a functional group represented by the following formula (1) in an amount of 0.55 to 5.5 mmol per gram of the sol:

$$MOS(=O)_2—R^1—Si(CH_3)_n(—O—)_{3-n} \qquad (1)$$

{wherein M is an alkyl group having 1 to 4 carbon atoms, a metal ion, or an ammonium ($NR^2_4$) group, $R^1$ is an alkylene group having 1 to 10 carbon atoms, $R^2$s, which may be the same or different, are each an alkyl group having 1 to 5 carbon atoms or a hydrogen atom, and n represents 0 or 1}.

2. The modified metal oxide sol according to claim 1, further comprising at least one silicon-based compound represented by the following formula (2):

$$X—(R^3)_m—Si(CH_3)_n(—Y)_{3-n} \qquad (2)$$

{wherein X is a functional group selected from the group consisting of linear or branched alkyl groups having 1 to 20 carbon atoms, a vinyl group, a thiol group, an amino group, a chlorine atom, an acrylic group, a methacrylic group, a styryl group, a phenyl group, a glycidoxy group, a 3,4-epoxycyclohexyl group, and a blocked isocyanate group, $R^3$ is an alkylene group having 1 to 5 carbon atoms, m is 0 or 1, Ys, which may be the same or different, each represent an alkoxy group having 1 to 4 carbon atoms or a hydroxyl group, and n represents 0 or 1}.

3. The modified metal oxide sol according to claim 1, further containing a metal alkoxide and/or an oligomer thereof.

4. The modified metal oxide sol according to claim 1, wherein the metal oxide sol is an organosilica sol.

5. A hydrophilizing agent, comprising the modified metal oxide sol according to claim 1.

6. A hydrophilic coating composition, comprising the modified metal oxide sol according to claim 1.

7. A structural body obtained by coating with the hydrophilic coating composition according to claim 6, and then curing the composition.

8. An antistatic agent, comprising a solid obtained by drying the modified metal oxide sol according to claim 1.

9. A structural body, comprising the antistatic agent according to claim 8.

* * * * *